United States Patent [19]
Li

[11] Patent Number: 6,102,934
[45] Date of Patent: Aug. 15, 2000

[54] ANCHOR TOOL AND METHOD AND APPARATUS FOR EMPLACING ANCHOR IN A BOREHOLE

[76] Inventor: Lehmann K. Li, 716 E. Broadway, Milford, Conn. 06460

[21] Appl. No.: 09/088,572

[22] Filed: Jun. 2, 1998

[51] Int. Cl.[7] .................................................. A61B 17/04
[52] U.S. Cl. ............................................................ 606/232
[58] Field of Search ............................ 606/232, 72–73, 606/228, 74–75

[56] References Cited

U.S. PATENT DOCUMENTS

| | | |
|---|---|---|
| 2,213,715 | 9/1940 | Monohan . |
| 4,741,330 | 5/1988 | Hayhurst . |
| 4,759,765 | 7/1988 | Van Kampen . |
| 4,776,330 | 10/1988 | Chapman et al. . |
| 4,823,794 | 4/1989 | Pierce ...................................... 606/232 |
| 4,898,156 | 2/1990 | Gatturna et al. . |
| 5,002,574 | 3/1991 | May et al. . |
| 5,163,946 | 11/1992 | Li . |
| 5,203,787 | 4/1993 | Noblitt et al. . |
| 5,217,486 | 6/1993 | Rice et al. . |
| 5,354,298 | 10/1994 | Lee et al. . |
| 5,372,604 | 12/1994 | Trott . |
| 5,443,482 | 8/1995 | Stone et al. . |
| 5,464,425 | 11/1995 | Skiba . |
| 5,464,427 | 11/1995 | Curtis et al. . |
| 5,486,197 | 1/1996 | Le et al. . |
| 5,531,792 | 7/1996 | Huene . |
| 5,540,718 | 7/1996 | Bartlett . |
| 5,545,180 | 8/1996 | Le et al. . |
| 5,569,303 | 10/1996 | Johnson . |
| 5,941,882 | 8/1999 | Jammet et al. ........................... 606/73 |

FOREIGN PATENT DOCUMENTS

| | | |
|---|---|---|
| 0270704 | 6/1988 | European Pat. Off. . |
| 2622430 | 5/1989 | France . |

Primary Examiner—Michael Buiz
Assistant Examiner—Vikki Hoa B. Trinh
Attorney, Agent, or Firm—Ostrolenk, Faber, Gerb & Soffen, LLP

[57] ABSTRACT

A method for emplacing a medical anchor in a borehole in biological tissue, the method comprising the steps of providing a borehole in the biological tissue, inserting the anchor into the borehole with a tool such that the anchor is affixed to the tool and in approximate alignment with the borehole, manipulating the tool, the step of manipulating the tool causing the anchor to pivot about an axis perpendicular to the borehole and further comprising rotating the anchor in the borehole about the axis of the borehole, thereby causing the anchor to move outwardly in the borehole to engage a wall of the borehole and cut into the wall of the borehole and secure the anchor in a final position in the borehole such that the anchor is disposed approximately perpendicular to the axis of the borehole; and removing the tool from the borehole by moving the tool proximally in the borehole, thereby separating the anchor from the tool and leaving the anchor secured in the borehole.

12 Claims, 14 Drawing Sheets

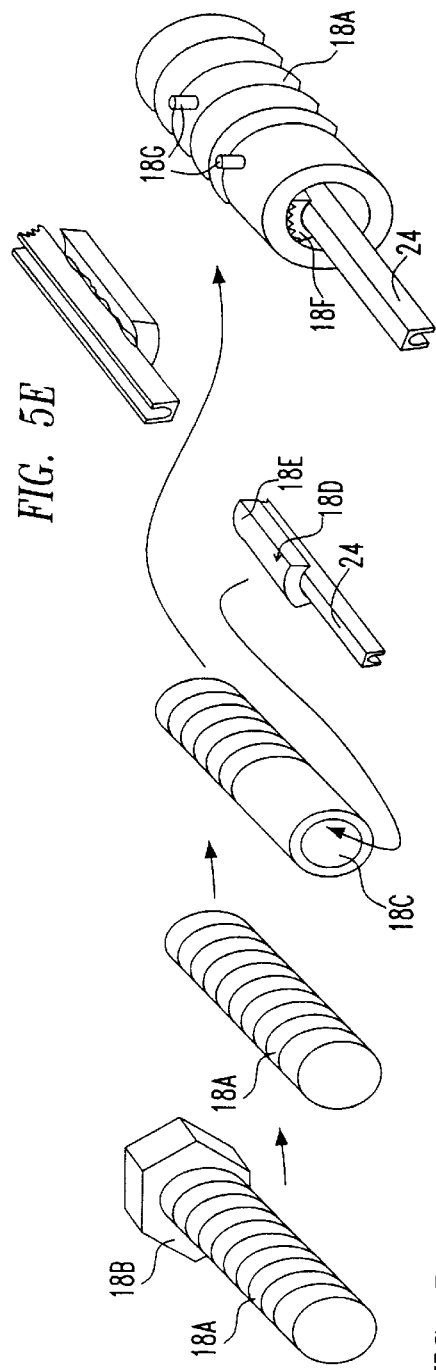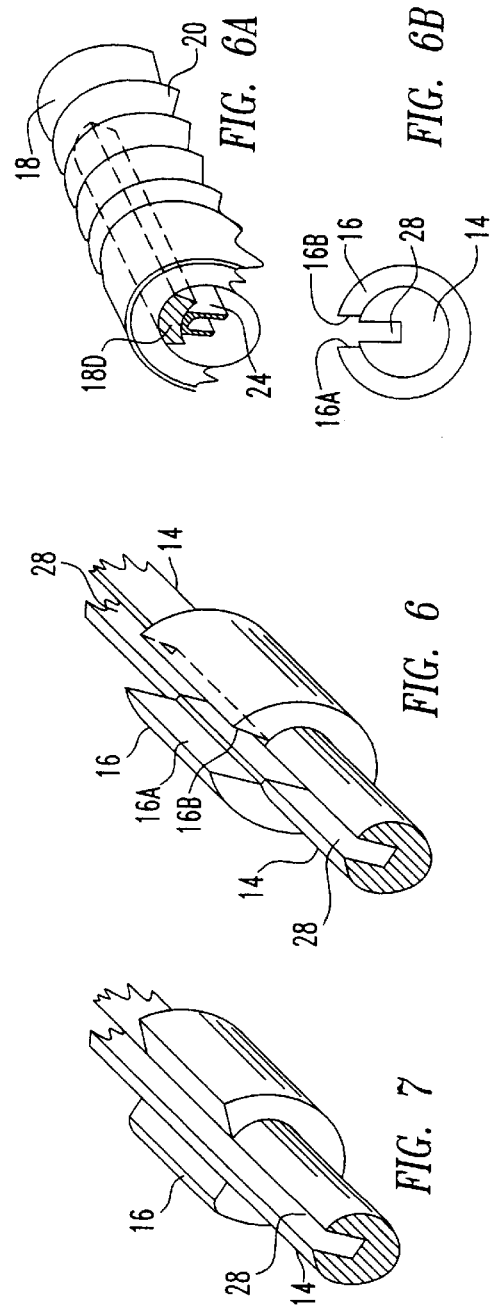

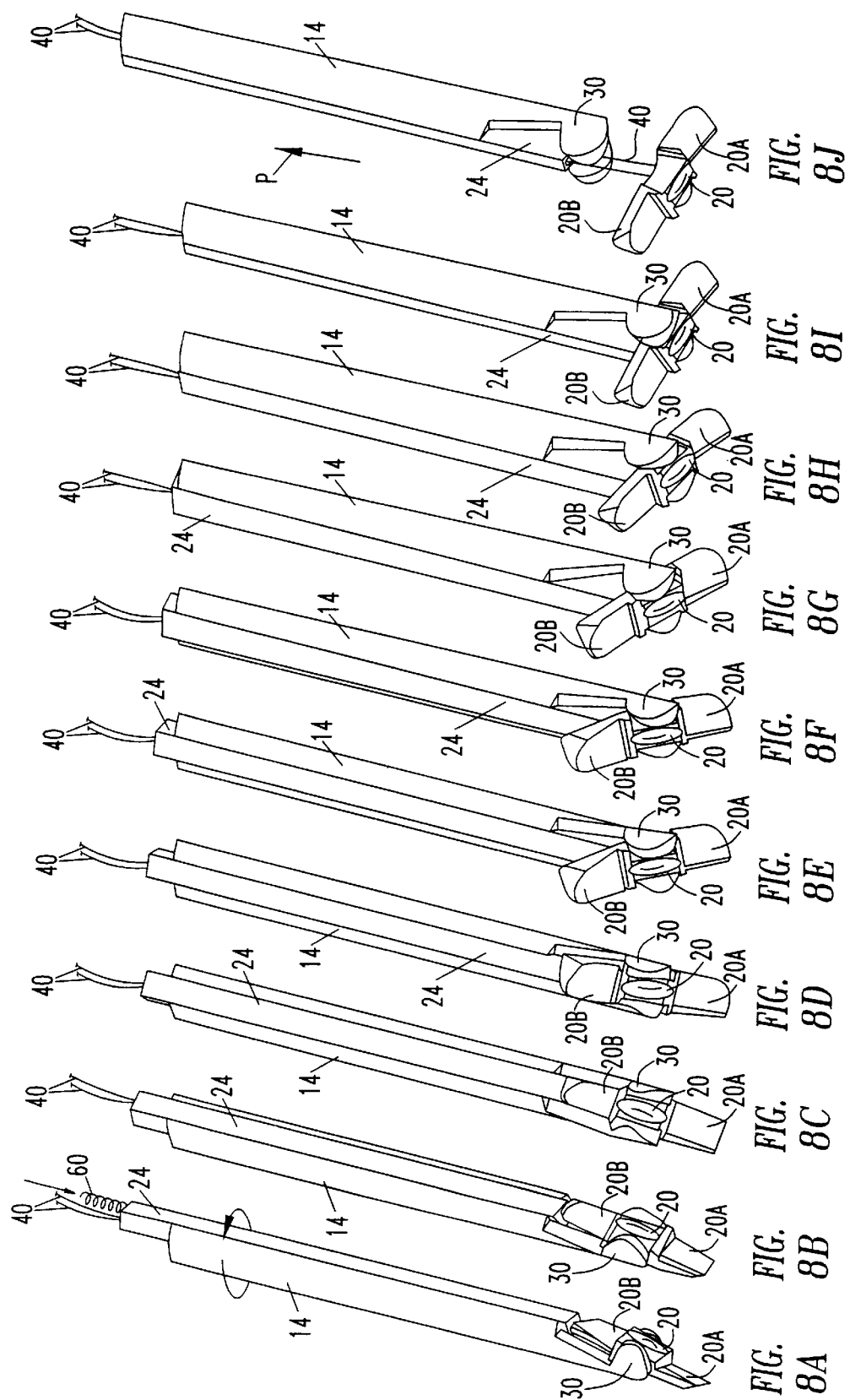

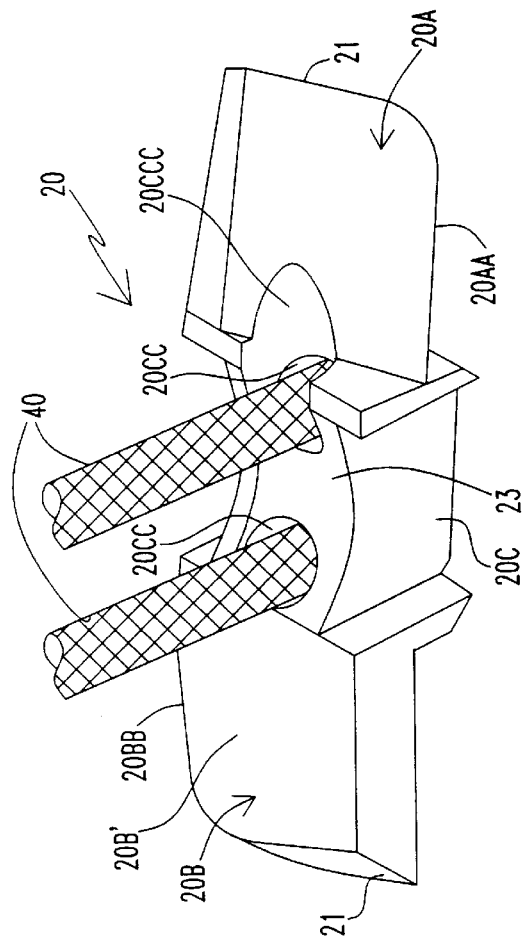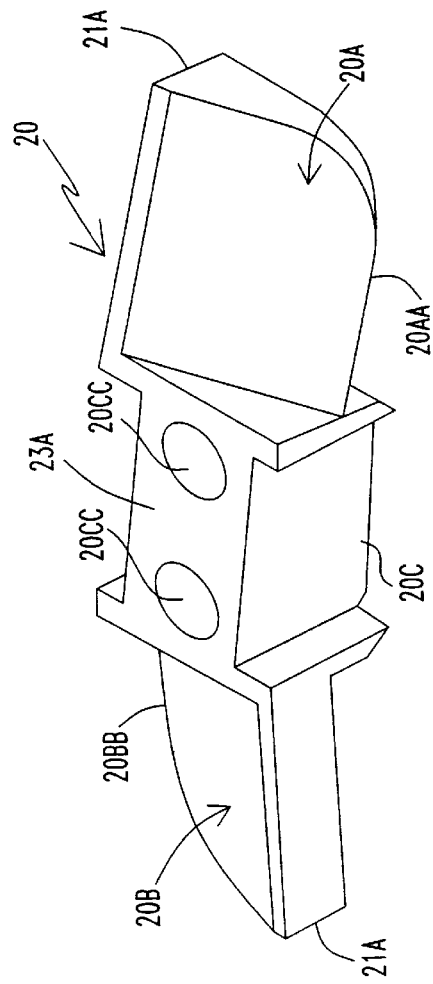

ANCHOR TOOL AND METHOD AND APPARATUS FOR EMPLACING ANCHOR IN A BOREHOLE

BACKGROUND OF THE INVENTION

The present invention relates to fixation devices or anchors and tools and methods for emplacing same. The present invention, in particular, relates to medical anchors, e.g., suture anchors or prosthesis anchors. It further relates to a method and apparatus for emplacing an anchor in biological material, for example, bone. Even more particularly, the present invention relates to a medical anchor which can be inserted through a longitudinally extending borehole so that the anchor is initially substantially aligned with the borehole and then, via an emplacement tool, manipulated so that the anchor pivots in two axes to form an undercut in the borehole and is secured substantially perpendicularly to the longitudinal extent of the borehole. The present invention is particularly suitable for the emplacement of anchors adapted to repair ligaments, e.g., rotator cuff ligaments, anterior cruciate ligaments (ACL's) and other ligaments. The anchor is also suitable for prosthesis fixation.

In Applicant's co-pending U.S. patent application Ser. No. 08/470,988, filed Jun. 6, 1995, a medical anchor is disclosed which can be emplaced in a groove which extends substantially parallel to the surface of the bone. The anchor of that patent application is placed in the groove, and then rotated along an axis defined by the tool (and which axis is perpendicular to the extent of the groove) to form an undercut in the walls of the groove in the bone to secure the anchor. The anchor of that application is suitable for repairing rotator cuff injuries, for example.

Applicant is also aware of U.S. Pat. No. 5,203,787 to Noblitt et al., in which a suture anchor can be emplaced in bone. This anchor is inserted in a longitudinally extending hole and then is twisted into place by manipulation of the sutures so that the suture anchor pivots along an axis which is perpendicular to the longitudinal axis of the borehole.

U.S. Pat. No 5,569,302 to Johnson describes an apparatus and method for attaching an object to bone in which a special tool is provided to form a groove which extends both longitudinally parallel to the bone and distally into the bone and a special tool is utilized to form an undercut into which the anchor is fitted.

The various prior art devices suffer from a number of defects. In the above-described co-pending patent application, although a securely emplaced anchor is obtained by using the device of that patent application, it is necessary to form a groove which extends essentially parallel to the surface of the bone. This is a more time consuming task than simply drilling a borehole. The Noblitt et al. device requires the manipulation of the sutures to emplace it, which may result in an unreliable emplacement, and furthermore, requires a complex manipulation. The Johnson reference requires a first tool for the formation of a specialized groove which extends both essentially parallel to the surface of the bone and distally into the bone and a another tool to form the undercut for the anchor. Accordingly, the Johnson device and method is unnecessarily complex.

There is a need in the medical art for an anchor which can be emplaced simply and which is securely fastened into the bone.

There is a need also for a tool for installing such an anchor with simple motions, and preferably one simple motion.

There is a need particularly for such an anchor which can be inserted into a simple longitudinally extending borehole, i.e., a drilled borehole, and which does not require complex, time consuming-to-make grooves or other specialized manipulations.

There is a need for an anchor which can be inserted into a borehole substantially in alignment with the borehole and once inserted, activated so that it engages with the walls of the borehole by moving to a position substantially perpendicular to the borehole.

Such an anchor would be suitable, for example, to repair rotator cuff and other ligament injuries such that the appropriate attachment strength is provided.

SUMMARY OF THE INVENTION

It is an object of the present invention to provide an anchor which can be easily emplaced and which provides sufficient strength for the attachment of prosthesis or sutures for the reattachment of, for example, ligaments, e.g., the rotator cuff or ACL ligaments.

Yet still a further object of the present invention is to provide an anchor which can be inserted in a distally extending borehole and which is adapted to be rotated in two axes so as to form an undercut in the borehole into which the anchor is secured.

Yet still a further object of the present invention is to provide such an which can be inserted longitudinally into a borehole and which can be emplaced so that the anchor rotates into an undercut which the anchor itself cuts into the borehole, the anchor rotating about one axis extending perpendicular to the borehole and another axis extending along the longitudinal axis of the borehole.

Yet still a further object of the present invention is to provide a tool for emplacing the described anchor and for performing the manipulations to form the undercut and secure the anchor in the borehole.

The above and other objects are achieved by a method for emplacing a medical anchor in a borehole in biological tissue, the method comprising the steps of providing a borehole in the biological tissue, inserting the anchor into the borehole with a tool such that the anchor is affixed to the tool and in approximate alignment with the borehole, manipulating the tool, the step of manipulating the tool causing the anchor to pivot about an axis perpendicular to the borehole and further comprising rotating the anchor in the borehole about the axis of the borehole, thereby causing the anchor to move outwardly in the borehole to engage a wall of the borehole and cut into the wall of the borehole and secure the anchor in a final position in the borehole such that the anchor is disposed approximately perpendicularly to the axis of the borehole; and removing the tool from the borehole by moving the tool proximally in the borehole, thereby separating the anchor from the tool and leaving the anchor secured in the borehole.

The above and other objects are also achieved by a medical anchor for emplacement in a borehole in a biological tissue member, the anchor comprising a central portion, at least one outer portion attached to the central portion, the outer portion having a cutting edge, the anchor being adapted to be inserted in the borehole in approximate alignment with a longitudinal axis of the borehole, and further being adapted to be rotated in two axes to secure the anchor in the borehole, a first axis of rotation being aligned with the axis of the borehole and a second axis of rotation being perpendicular to the axis of the borehole, whereby the anchor moves outwardly about the second axis so that the cutting edge cuts into a wall of the borehole and the anchor is rotated about the first axis to achieve a final position substantially perpendicular to the borehole.

The above and other objects are furthermore achieved by an apparatus for emplacing a medical anchor in a borehole in biological tissue the anchor comprising a member having at least one portion adapted to cut into a wall of the borehole to secure the anchor in the borehole, the apparatus comprising a handle having a gripping surface, a shaft having a first longitudinal axis, the shaft being attached to the handle and having a distal end for insertion in the borehole, the distal end having a pivoting receptacle for receiving the anchor initially in a position approximately aligned with the first axis, a pushing member movable distally with respect to the shaft to push on the anchor in the pivoting receptacle, the shaft being rotatable about the first axis, the pushing member being movable distally with respect to the shaft to rotate the anchor in the pivoting receptacle about a second axis substantially perpendicular to the shaft, thereby causing the at least one portion of the anchor to move outwardly and cut into the wall of the borehole to secure the anchor in the borehole, the anchor rotating about said first and second axes to secure the anchor in the borehole with the anchor being secured in a final position approximately perpendicular to the first axis.

The above and other objects of the present invention are also achieved by an apparatus for emplacing a medical anchor in a borehole in biological tissue, the anchor comprising a member having two opposed portions adapted to cut into walls of the borehole to secure the anchor in the borehole, the apparatus comprising a handle having a gripping surface, a shaft having a first longitudinal axis, the shaft being attached to the handle and having a distal end for insertion in the borehole, the distal end having a pivoting receptacle for receiving the anchor initially in a position approximately aligned with the first axis, a pushing member disposed in a channel in the shaft, the pushing member being slidably movable distally in the shaft to push on the anchor in the pivoting receptacle, a slidable collar disposed slidably on the shaft and attached to the pushing member, the slidable collar being movable distally on the shaft as the shaft is rotated about the first axis to cause the pushing member to move distally to rotate the anchor in the pivoting receptacle about a second axis substantially perpendicular to the shaft, thereby causing the two opposed portions of the anchor to move outwardly and cut into the walls of the borehole to secure the anchor in the borehole, the anchor rotating simultaneously about said first and second axes to secure the anchor in the borehole with the anchor being secured in a final position approximately perpendicular to the first axis.

The above and other objects are furthermore achieved by an anchor for emplacement in a borehole in a biological tissue, the anchor comprising, a cutting member having, a central portion having a securement point for a prosthesis; and at least one outer portion attached to the central portion, the outer portion having a cutting edge, a pivoting receptacle for the cutting member comprising a carrier member, the carrier member being receiving in a support washer, the support washer having a region for engaging a surface of the tissue surrounding the borehole, the anchor being adapted to be inserted in the borehole with the cutting member in approximate alignment with a longitudinal axis of the borehole, and further wherein the cutting member is adapted to be rotated in two axes to secure the anchor in the borehole, a first axis of rotation being aligned with the axis of the borehole and a second axis of rotation being perpendicular to the axis of the borehole, whereby the cutting member moves outwardly about the second axis so that the cutting edge cuts into a wall of the borehole and the anchor is rotated about the first axis to achieve a final position substantially perpendicular to the borehole.

The above and other objects are also achieved by an apparatus for repairing a ligament or installing a ligament replacement, the apparatus comprising, a first anchor attached to a first end of the ligament or ligament replacement, a second anchor attached to a second end of the ligament or ligament replacement, the first and second anchors being attached to the respective first and second ends by suture, the first and second anchors with the ligament or ligament replacement being insertable through a first borehole disposed in a first bone member into an aligned borehole in a second bone member such that the first anchor is disposed in the aligned borehole and the second anchor is disposed in the first borehole, the first anchor being rotatable about two axes in the aligned borehole, one axis being perpendicular to the aligned borehole and the other axis being aligned with the aligned borehole, the first anchor attaining a final position substantially perpendicular to the aligned borehole such that the first anchor penetrates the wall of the aligned borehole to secure the first anchor in the aligned borehole and the second anchor being rotatable in two axes in the first borehole, one axis being perpendicular to the first borehole and the other axis being in alignment with the first borehole, the second anchor attaining a final position substantially perpendicular to the first borehole such that the second anchor penetrates the wall of the first borehole to secure the second anchor in the first borehole, thereby securing the ligament or ligament replacement between the first and second bone members.

The above and other objects are also achieved by a method for repairing a ligament or installing a ligament replacement, the method comprising the steps of, providing a first anchor attached to a first end of the ligament or ligament replacement, providing a second anchor attached to a second end of the ligament or ligament replacement, the first and second anchors being attached to the respective first and second ends by suture, inserting the first and second anchors with the ligament or ligament replacement with an insertion tool through a first borehole disposed in a first bone member into an aligned borehole in a second bone member such that the first anchor is disposed in the aligned borehole and the second anchor is disposed in the first borehole, rotating the first anchor with the insertion tool about two axes in the aligned borehole, one axis being perpendicular to the aligned borehole and the other axis being aligned with the aligned borehole and obtaining a final position of the first anchor substantially perpendicular to the aligned borehole such that the first anchor penetrates the wall of the aligned borehole to secure the first anchor in the aligned borehole, rotating the second anchor with the insertion tool about two axes in the first borehole, one axis being perpendicular to the first borehole and the other axis being in alignment with the first borehole, and obtaining a final position of the second anchor substantially perpendicular to the first borehole such that the second anchor penetrates the wall of the first borehole to secure the second anchor in the first borehole, thereby securing the ligament or ligament replacement between the first and second bone members and removing the insertion tool.

The above and other objects are also achieved by an apparatus for repairing a ligament or installing a ligament replacement, the apparatus comprising: an anchor attached to a first end of the ligament or ligament replacement, the anchor being attached to the first end by suture, the anchor with the ligament or ligament replacement attached thereto being insertable into a borehole disposed in a bone member such that the anchor is disposed in the borehole initially substantially in alignment with the borehole, the anchor being rotatable about two axes in the borehole, one axis being perpendicular to the borehole and the other axis being aligned with the borehole, the anchor attaining a final position substantially perpendicular to the borehole such that the anchor penetrates the wall of the borehole to secure the anchor with the ligament or ligament replacement attached thereto in the borehole.

The above and other objects are further achieved by a method for repairing a ligament or installing a ligament replacement, the method comprising the steps of: providing an anchor attached to a first end of the ligament or ligament replacement, the anchor being attached to the first end by suture, inserting the anchor with the ligament or ligament replacement attached thereto with an insertion tool into the borehole in a bone member such that the anchor is disposed initially substantially in alignment with the borehole, rotating the anchor with the insertion tool about two axes in the borehole, one axis being perpendicular to the borehole and the other axis being aligned with the borehole and obtaining a final position of the anchor substantially perpendicular to the borehole such that the anchor penetrates the wall of the borehole to secure the anchor with the ligament or ligament replacement attached thereto in the borehole.

Other objects, features and advantages of the present invention will be apparent from the detailed description which follows.

BRIEF DESCRIPTION OF THE DRAWINGS

FIGS. 5A–5F show one manner of forming some of the components of the anchor emplacement tool according to the present invention;

FIG. 6 shows a perspective detail of the emplacement tool;

FIG. 6A is a perspective partial view showing a detail of the emplacement tool according to the present invention;

FIG. 6B is an end view of FIG. 6;

FIG. 7 is an alternative embodiment of a portion of the emplacement tool;

FIGS. 8A–8J show, in perspective views, details of the distal portion of the tool as it is emplacing an anchor in a borehole, with the borehole not shown;

FIG. 10 is a perspective view of the anchor according to the present invention with sutures attached thereto;

FIG. 11 is a perspective detailed view of a modified form of the anchor according to the present invention;

DETAILED DESCRIPTION OF EMBODIMENTS OF THE INVENTION

Figure 1:
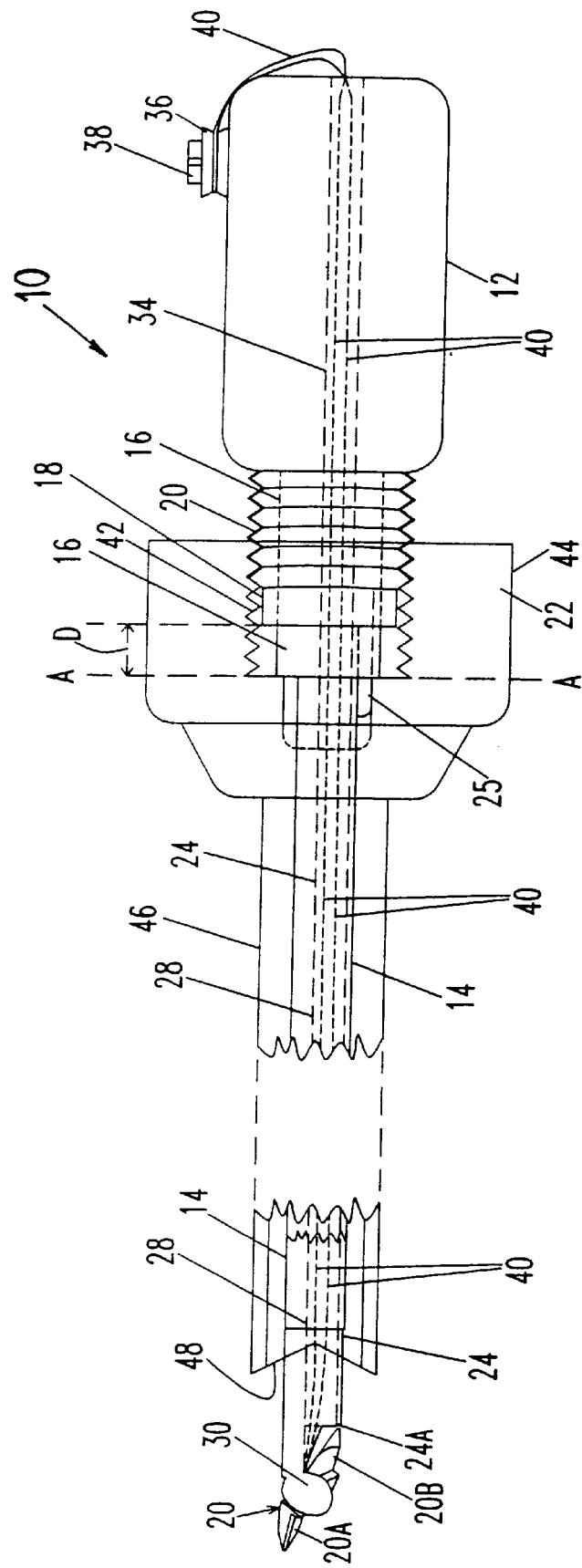
FIG. 1 is a partially cutaway plan view of an emplacement tool according to the present invention for emplacing the anchor according to the present invention.
Figure 2:
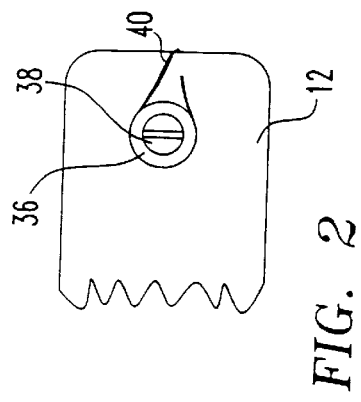
FIG. 2 is a plan detail of FIG. 1.

With reference now to the drawings, FIG. 1 is a partially cutaway plan view of a tool for emplacing an anchor, e.g., a medical anchor such as a suture anchor or prosthesis anchor. The tool is generally indicated at 10. The anchor emplaced by the tool is shown at 20 and in this embodiment, comprises a suture anchor. The tool comprises a handle 12, a longitudinally extending central hollow shaft 14 which is secured to the handle 12, a collar 16 which is provided fixed on the shaft 14 and turns with the shaft 14 and is disposed adjacent to handle 12, and an exteriorly threaded sliding collar 18 which is slidable upon the collar 16 of shaft 14. Collar 18 has a threaded portion 20. Collar 18 is adapted to slide on the collar 16 of shaft 14.

Figure 1A:
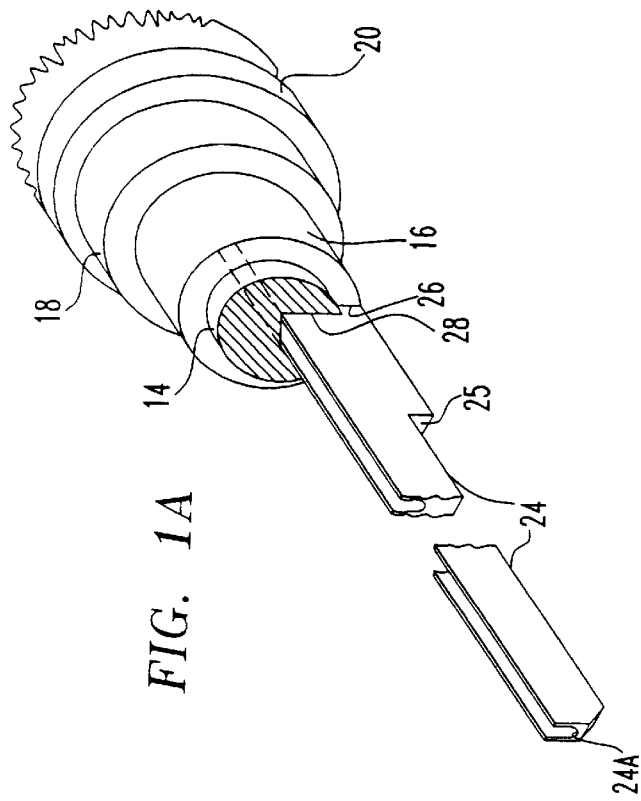
FIG. 1A is a perspective detail of FIG. 1.
Figure 9:
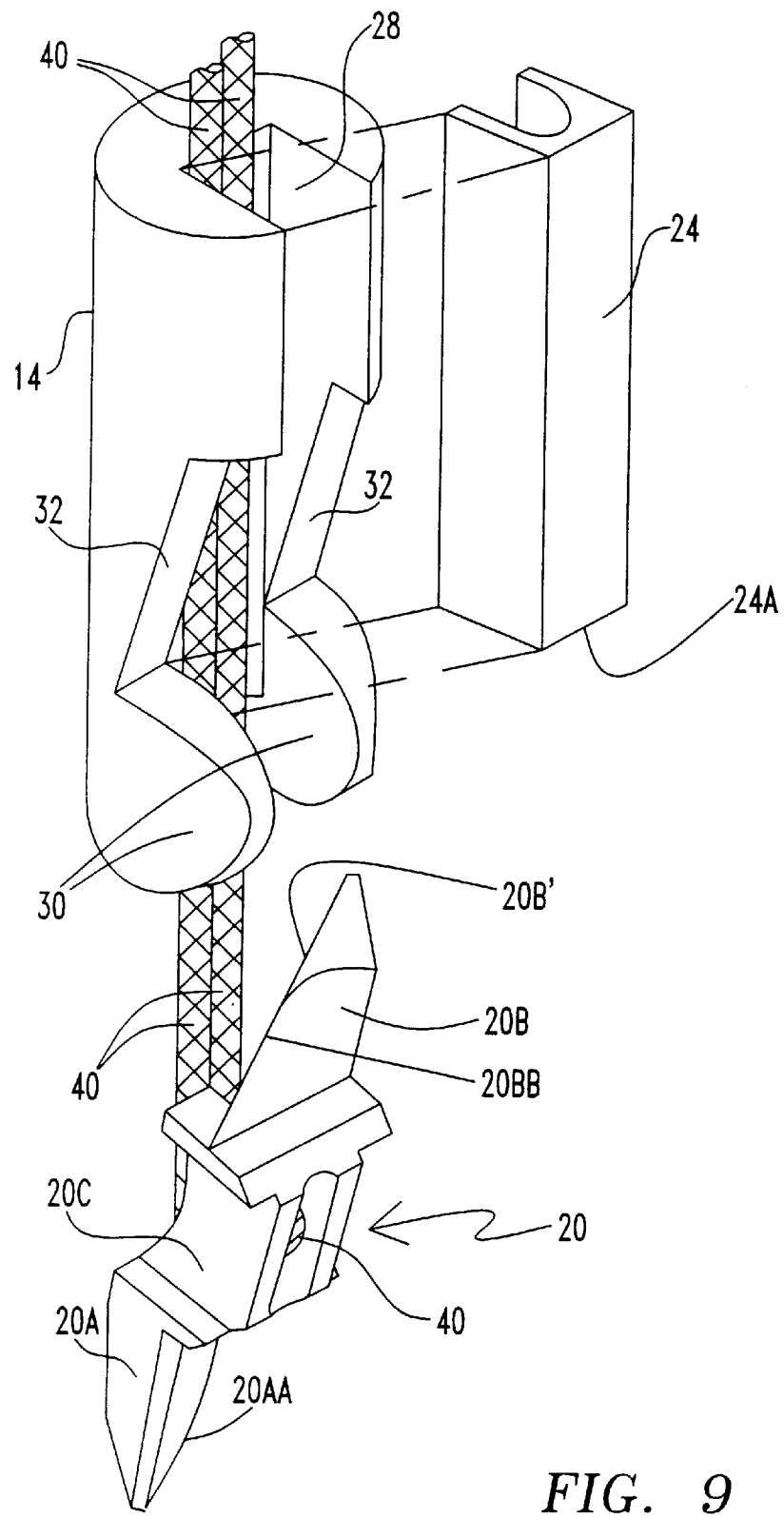
FIG. 9 is an exploded perspective view of the distal end of the emplacement tool and the anchor.

The threads 20 of collar 18 are threadably received in an external gripping member 22 which is provided with handgrips to be grasped by a surgeon's hand. Collar 18 has fixedly attached thereto for movement therewith a pushing channel 24. See FIGS. 1A and 4. Pushing channel 24 is slidable within a slot 26 provided in the collar 16. The pushing channel 24 further extends throughout and is slidable in a channel 28 provided in the shaft 14. See FIG. 4. The shaft 14 terminates in a pivoting receptacle 30 at the distal end. The shaft 14 at the distal end has cutouts 32 serving as a seat for the anchor 20 during initial insertion so that the anchor is initially approximately aligned with the longitudinal axis of shaft 14. The anchor 20 is approximately disposed along the longitudinal axis of shaft 18 during initial insertion, although at a slight angle with respect to the axis of shaft 14. See FIG. 1 and FIG. 9. The anchor 20 according to the invention, which will be described in greater detail below, is thus received in the pivoting receptacle 30 during initial insertion into a borehole such that it is approximately aligned with the borehole, facilitating insertion. The anchor 20 preferably includes two opposed blade portions 20A and 20B which are adapted to cut into bone when the anchor 20 is rotated in two axes, to be explained in greater detail below.

Figure 4:
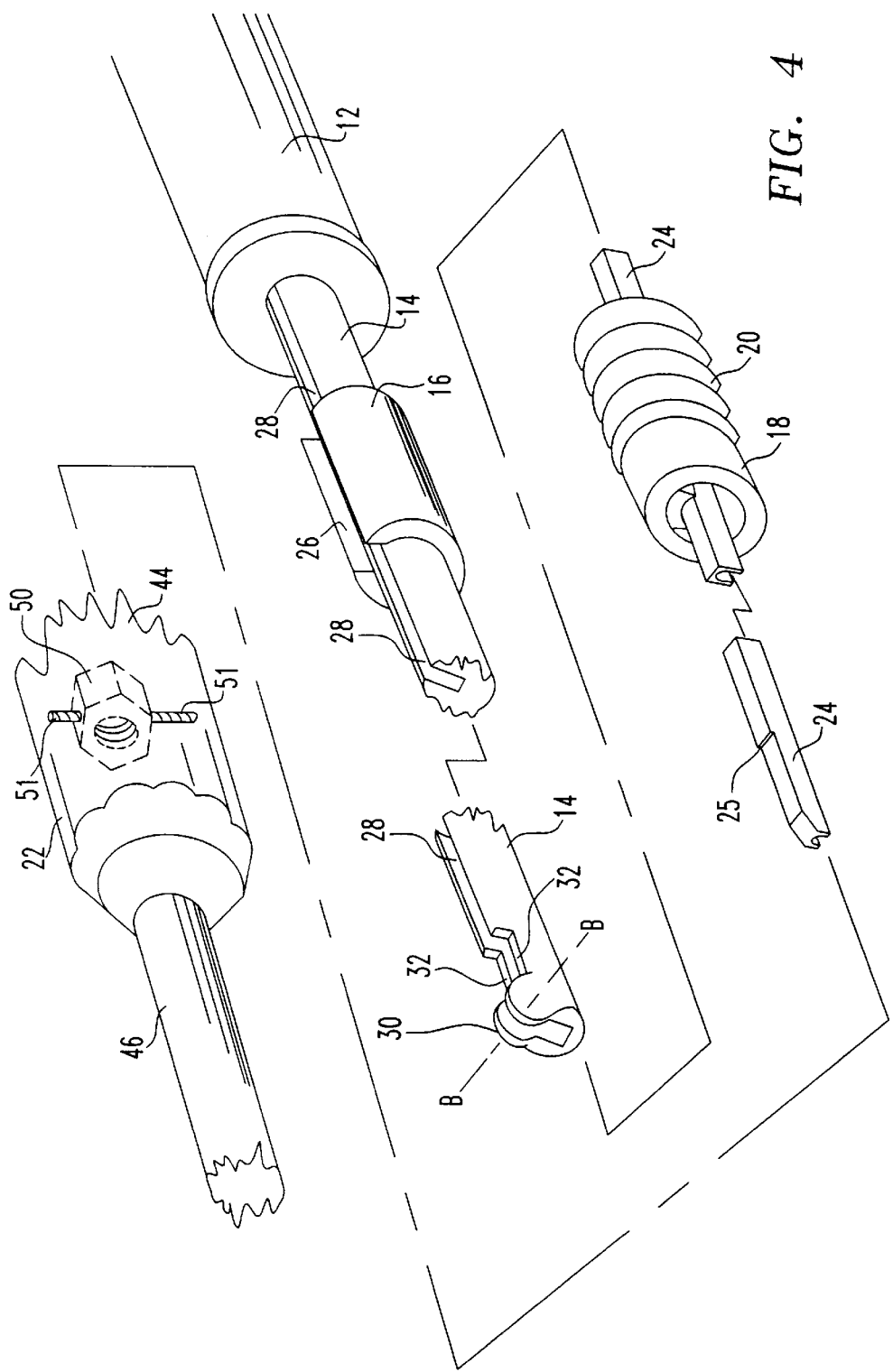
FIG. 4 is a perspective exploded view of the anchor emplacement tool according to the present invention.

The pushing channel 24 is adapted to push against a cam surface of the anchor 20 to allow it to rotate in the axis of the receptacle indicated by line B—B of FIG. 4. At the same time, rotation of the handle 12 rotates the anchor 20 about the axis of the borehole, securing the anchor in the borehole. This will be described in further detail below. Although the anchor shown is a suture anchor, it may be a prosthesis anchor and emplaced to secure a prosthesis in, e.g., bone. Additionally the anchor 20 shown has two portions 20A and 20B. However, an anchor according to the invention can be provided having only one portion 20A having a single cutting edge for cutting into the wall of a borehole to secure the anchor.

The pushing channel 24 is preferably provided as a channel so that if the anchor 20 comprises a suture anchor, the sutures 40 which are threaded through the suture anchor 20 can extend through the channel 24 in shaft 14 and through a longitudinally extending channel 34 provided in the handle 12. The sutures are then conveniently tensioned by twisting them around a holding member, e.g., a flexible plastic or rubber grommet 36 which is secured on the handle 12 by a screw 38. The sutures are indicated by the lines 40. Pushing channel 24 may reduce in thickness as shown at 25.

Gripping member 22 is internally threaded with threads 42 which threadingly engage with threads 20 of the slidable collar 18 and is provided with a suitable gripping surface 44. The gripping member 22 is provided so that the shaft 14 can rotate therein. Gripping member 22 is coupled to a further shaft 46 which is disposed concentrically about shaft 14. Shaft 46 terminates with a "V" shaped end 48. The purpose of "V" shaped end 48 is to provide a surface which will engage with the bone surface surrounding a borehole to maintain the tool in position during emplacement of the anchor and to maintain the anchor at the desired emplacement depth in the borehole. This will be explained in greater detail below. See also FIGS. 12A and 12B.

Figure 3:
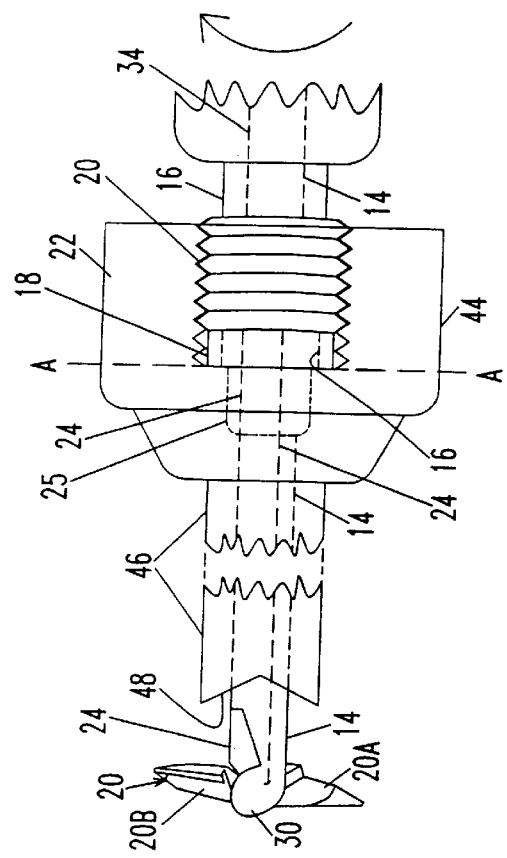
FIG. 3 is a plan detail of FIG. 1.

As shown by comparing FIGS. 1 and 3, and reviewing FIGS. 8A–8J, the anchor 20 is emplaced as follows. The surgeon inserts the tool, with the anchor 20 received in the pivoting receptacle 30 at the distal end thereof and generally aligned with the axis of the tool, into a predrilled borehole in the bone. The anchor 20 at this time is approximately directed along the axis of the shaft 14. See FIG. 8A, which corresponds to FIG. 1. The sutures 40, as explained previously, are looped through apertures in the suture anchor 20 and extend through the pushing channel 24 which is disposed in the interior of hollow shaft 14. See FIG. 10. The sutures then extend through the handle 12 and are suitably tensioned by grommet 36, holding the suture anchor 20 securely in pivoting receptacle 30.

Once the tool with the anchor 20 has been placed at the desired depth in the borehole in the bone, as determined by the distal location of end 48 of shaft 46, the surgeon holds the gripping member 22 stationary in one hand and turns the handle 12, also provided with a gripping surface, with the other hand. Alternatively, other embodiments of the tool can be developed whereby the tool can be operated with one hand. This manipulation causes the shaft 14 to rotate, imparting this rotation to pusher channel 24 disposed in channels 26 and 28, which in turn imparts the rotation to collar 18. The threads 20 on collar 18 thus move with respect to the threads 42 of the stationary gripping member 22. The entire threaded collar 18 thus slides on the collar 16 of shaft 14. The movement of the collar 18 in the gripping member 22 will cause the pushing channel 24, which is affixed to the collar 18, to move toward the distal end. The distal end 24A of the pushing channel 24 is in engagement with a cam surface of the anchor 20. As the collar 18 moves distally with respect to the gripping member 22, and thus with respect to the shaft 14, the pushing channel 24 also moves distally, causing the anchor 20 to pivot about line B—B in the receiving receptacle 30. At the same time, since the shaft 14 is rotating, the anchor 20 cuts into the bone as it moves radially outwardly. The anchor rotates in two axes: one axis along line B—B as it is forced outwardly by pushing channel 24 and a second axis aligned with the axis of shaft 13 as shaft 14 is rotated. The anchor thus moves in a spiral path as it expands radially outwardly and cuts into the bone due to the combined action of shaft 14 turning and pusher channel 24 moving distally.

The anchor 20 has cutting surfaces 20AA and 20BB disposed on opposite portions of the respective anchor portions 20A and 20B. See FIG. 10. As the shaft 14 rotates and the pushing channel 24 moves distally, the anchor 20 executes a spiral motion as the portions 20A and 20B begin to move radially outwardly cutting into the wall of the borehole in the bone. The shaft 14 may turn through approximately 90 to 180°, depending upon the amount the handle 12 is turned and the distance D (FIG. 1) through which the threaded collar 18 can move with respect to the gripping member 22. Compare FIGS. 1 and 3.

FIG. 4 shows an embodiment of the anchor emplacement tool according to the invention wherein a nut 50 has been embedded in the gripping member 22 to provide the internal threads 42 with which threads 20 of the threaded collar 18 engage. FIG. 1 shows the member 22 with internally formed threads 42 formed integrally with the member 22. Alternatively, an internally threaded insert can be provided in the member 22 to form the threads 42. In FIG. 4, the nut 50 is pinned into position in the gripping member 22 as shown by pins 51.

FIGS. 5A–5B show one method of making the threaded collar 18. Threaded collar 18 may be made from a bolt 18A. The head 18B of the bolt 18A is cut off as shown in FIG. 5B. A bore 18C is formed concentrically in the threaded bolt 18A. A key 18D is formed having a curved surface 18E. The key 18D has the pushing channel 24 welded thereto. The surface 18E of the key 18 is thereafter welded and/or pinned, as shown at 18F and 18G, to the drilled, threaded bolt 18A. The threaded collar 18 thus turns with the pushing channel 24 as the pushing channel 24 turns with rotating shaft 14. As shaft 14 turns, the collar 18 moves in the threads of gripping member 22. As explained, the pushing channel 24 thus moves distally as it rotates in the rotating shaft 14, causing the anchor 20 to pivot in the pivoting receptacle 30 about axis B—B, thus extending radially outwardly as the shaft 14 turns. The anchor 20 spirals radially outwardly as the cutting edges of the anchor undercut into the walls of the borehole. The anchor thus undergoes two pivoting motions: about line B—B of receptacle 30 and along the axis of shaft 14.

FIG. 7 shows an alternative embodiment of the collar 16. In the embodiment of FIG. 6, the collar 16 has vertically cut surfaces 16A and 16B which assist in imparting the rotation of the shaft 14 to the threaded collar 18 through key 18D. In the embodiment of FIG. 7, only the vertical walls of the channel 28 impart the rotation of the shaft 14 to the pushing channel 24 which in turn imparts rotation to the threaded collar 18. Accordingly, the embodiment of FIG. 6 is somewhat stronger than the embodiment shown in FIG. 7.

FIGS. 8A–8j show the steps employed in emplacing the anchor 20. The shaft 14 with the anchor 20 mounted in the pivoting receptacle 30 is inserted in the borehole into the bone, not shown. The handle 12 is turned while the gripping member 22 remains stationary. This turning motion causes the shaft 14 to rotate as shown in FIGS. 8A–8j. While the shaft 14 is rotating, the rotation of the shaft is imparted to the pushing channel 24 and key 18D which is in turn imparted to the threaded collar 18. The threaded collar 18 is threaded in the gripping member 22 and accordingly, it slides on the collar portion 16 which is affixed to shaft 14. This causes the threaded collar 18 to slide on the shaft 14, causing the pushing channel 24 to move distally. The distal end 24A of the pushing channel 24 cams against the anchor 20 cam surface 20B' (FIGS. 9 and 10), causing it to spiral out radially as the shaft 14 is turned.

The cutting edges 20AA and 20BB of anchor 20 cut into the walls of the borehole to secure the anchor into the borehole. Once secured, the sutures 40 are released from tensioning grommet 30 and the tool 10 is moved in the proximal direction as shown by the arrow P in FIG. 8J, causing the secured anchor 20 to detach from the pivoting receptacle 30 in which it is held. The tool 10 is pulled out of the borehole and clear of the sutures 40, leaving the anchor 20 with the sutures attached to the anchor in the bone. A detached ligament or a prosthesis can then be secured to the sutures 40.

As also shown in FIG. 8A, a spring 60 may be provided to impart downward pressure on the pusher channel 24, in accordance with the embodiment of the tool shown in FIG. 14 to be described below.

FIG. 10 shows details of a suture anchor 20. As shown, the suture anchor includes two opposed portions 20A and 20B. Portion 20A has cutting edge 20AA and portion 20B has cutting edge 20BB disposed on opposite sides of the anchor. Between the portions 20A and 20B, a central portion 20C is disposed having two openings 20CC through which the suture 40 is looped. To assist in looping the sutures through the openings 20CC, a sloping surface 20CCC may be provided as shown. Similarly, a surface to assist the suture through the other opening 20CC may be provided on the bottom side of the anchor 20, not shown.

FIG. 11 shows an alternative embodiment of the anchor 20. Unlike the embodiment of FIG. 10, which has angled sidewalls 21, this anchor has substantially vertical sidewalls 21A as shown and a flat upper surface of the central portion 20C, as indicated at 23A, in contrast to the curved surface 23 of the anchor of FIG. 10.

Figure 12B:
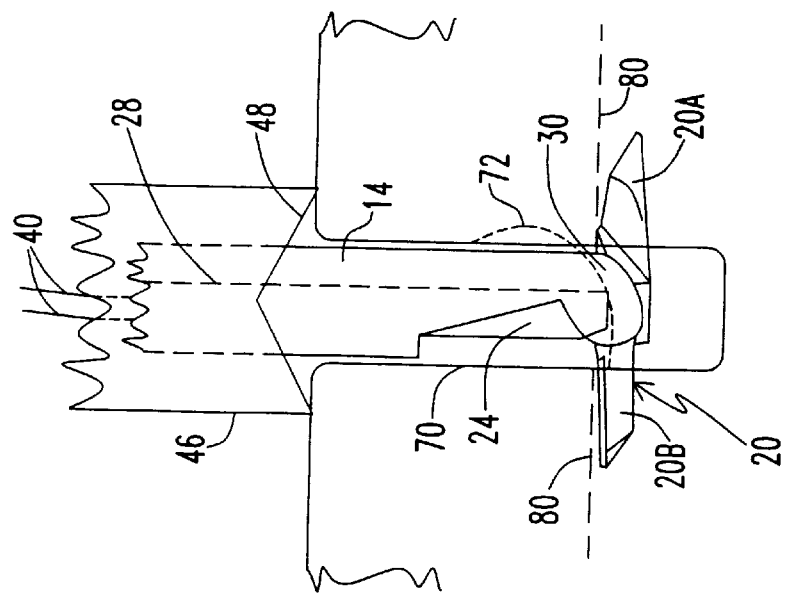
FIGS. 12A & 12B show the beginning and ending steps employed in emplacing the anchor according to the present invention.
Figure 12A:
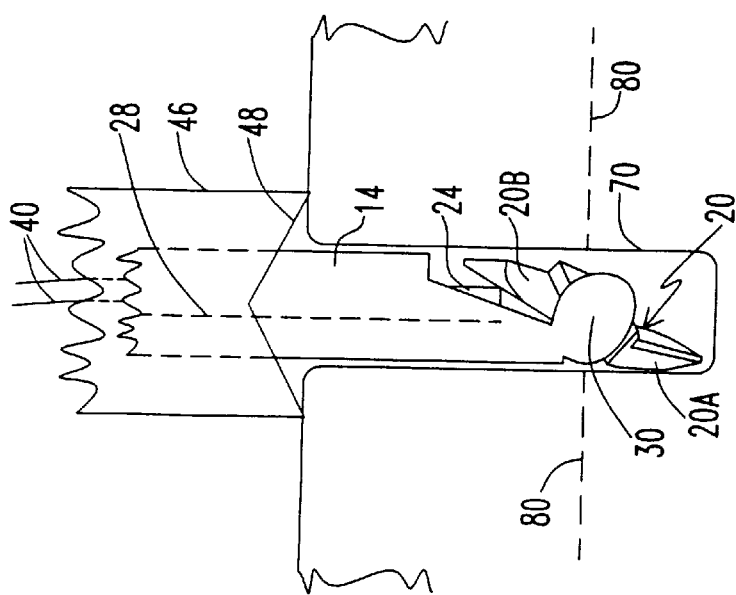

FIGS. 12A and 12B show the beginning and ending steps of emplacing the anchor. FIG. 12 shows the beginning step where the shaft 14 is emplaced in the bore hole 70 in bone. FIG. 12A corresponds to FIG. 8A. FIG. 12B corresponds to FIG. 8I. Once the anchor 20 has been emplaced in the self-made undercut, as shown in FIG. 12B, the shaft 14 is withdrawn, as shown in FIG. 8J. The spiral movement of the anchor 20 as it is emplaced is shown by dashed curved line 72.

Although the anchor of the present invention is adapted to cut into both the harder cortical bone layer and the softer sub-cortical cancellous region, one preferred method of emplacing the anchor comprises emplacing the anchor so that it has a final position, as shown in FIG. 12B, wherein the anchor is disposed perpendicular to the borehole just below the cortical layer. The transition from cortical to sub-cortical regions is shown by dashed line 80 in FIG. 12B. By pulling the tool, and thus the anchor, in the proximal direction, the surgeon can be assured that the anchor is secured just below the cortical region.

Figure 13:
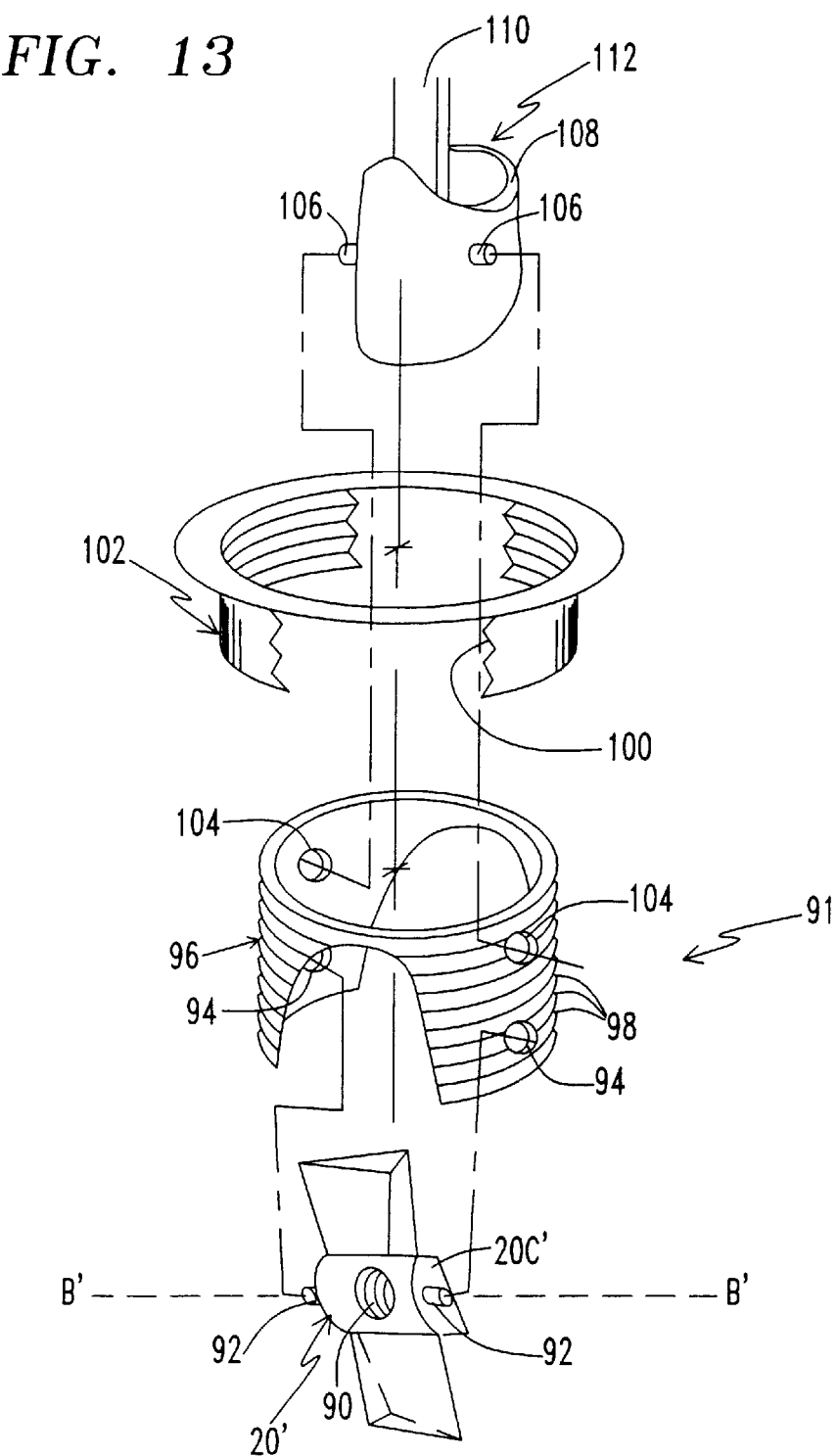
FIG. 13 shows a prosthesis anchor according to the present invention and a tool for emplacing the anchor.

FIG. 13 shows a prosthesis anchor 91 which has an anchor member 20' which is substantially the same as the suture anchor 20 of FIGS. 10 and 11 except that in the central portion 20C', the prosthesis anchor member 20' has a threaded opening 90 instead of openings for looping a suture therethrough. In addition, the prosthesis anchor member 20' includes two pivot projections 92, which are received in openings 94 of a carrier 96. The carrier 96 is provided with ratcheting or gripping serrations 98 on its exterior surface which are adapted to be received in mating serrated interior surface 100 of a shouldered washer 102. The carrier 96 is additionally provided with torque transmission openings 104 which are adapted to receive torque transmission projections 106 on a cylindrical member 108 of an inserter tool 112. The inserter tool 112 includes a pusher member 110 which is similar to the pushing channel 24 of the tool of FIG. 1 and serves the same function of camming against the anchor member 20' to rotate the anchor member about axis B'—B' of FIG. 13.

Figure 13A:
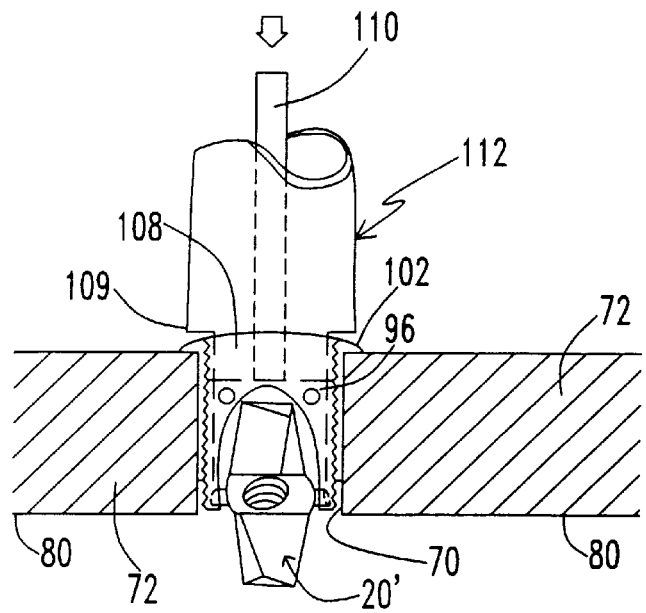
FIGS. 13A, 13B and 13C show steps in the emplacement of the anchor of FIG. 13 using the tool of FIG. 13.
Figure 13B:
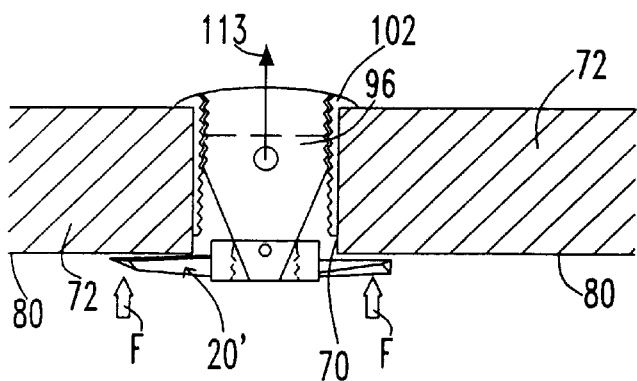
Figure 13C:
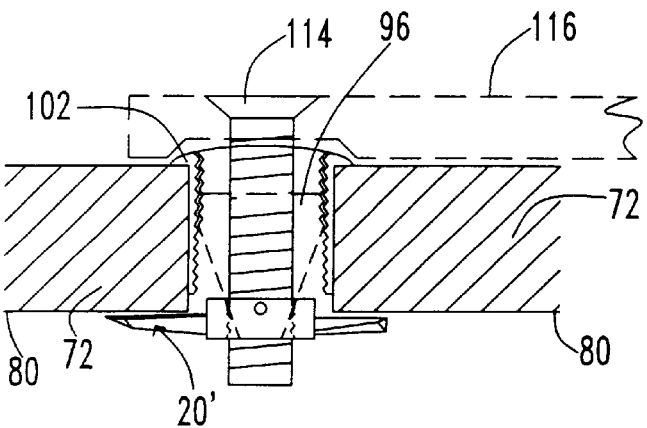

As shown in FIGS. 13A–13C, the anchor 91 of FIG. 13 is emplaced as follows: The carrier 96 with anchor member 20' attached in the pivoting openings 94 of carrier 96 is secured in the washer 102. The serrations 98 and 100 allow the carrier 96 to be snapped into the washer 102 so that the carrier 96 detents into a desired position in the washer 102. The inserter tool 112 is thereafter secured in the washer 102 such that the projections 106 are received in the openings 104 of the carrier 96. The projections 106 are radially movable by a mechanism not shown so that they can be inserted into the washer 102 and move into position, for example, by snapping into position against spring pressure into the openings 104 in the carrier 96. As discussed, the projections 106 are provided as torque transmission means so that when the tool 112 is rotated, the carrier 96 with the anchor member 20' affixed thereto rotates along the axis of the tool 112. Tool 112 may otherwise be the same as the tool 10 shown in FIG. 1, having only a different distal end, as shown in FIG. 13. Otherwise, the tool operates in the same way to move the pusher member 110 distally while the tool is rotated.

As shown in FIG. 13A, the tool, generally shown at 112 with the end 108 having the carrier 96, washer 102 and anchor member 20' attached thereto, is inserted into the borehole 70 in the bone 72. As shown, the anchor member 20' is substantially aligned initially with the axis of the tool. Thereafter, the tool 112 is rotated. This rotation, as in the embodiment of FIG. 1, causes the pusher member 110 to move distally, thus causing the anchor member 20' to rotate about the axis B'—B' at the same time that it rotates about the axis of the tool 112. This causes the anchor member 20' to move outwardly and cut into the wall of the borehole, eventually obtaining the final position shown in FIG. 13B. As shown in FIG. 13B, the anchor member has been emplaced directly below the cortical layer of the bone. The transition between cortical and subcortical bone is shown by line 80. In order to ensure that the anchor member is secured below the cortical layer, a force F in the proximal direction, as shown by the arrows F, may be applied to the anchor by pulling up on the tool 112 as shown by arrow 113. At the same time, a shoulder 109 of the tool 112 bears down on the washer 102 to prevent the washer 102 from pulling out of the borehole. The carrier 96 may move upwardly in the serrations 100 of the washer 102 and detent into position in the washer 102 to apply tension to the anchor member 20'. The tool is then actuated to release the projections 106 from the openings 104, thereby releasing the tool 112 from the anchor 91.

Thereafter, a screw 114 may be threaded into the threaded aperture 90 in the anchor member 20' to secure a prosthesis or any other device, such as the bone plate 115 shown, to the bone 72.

Figure 14:
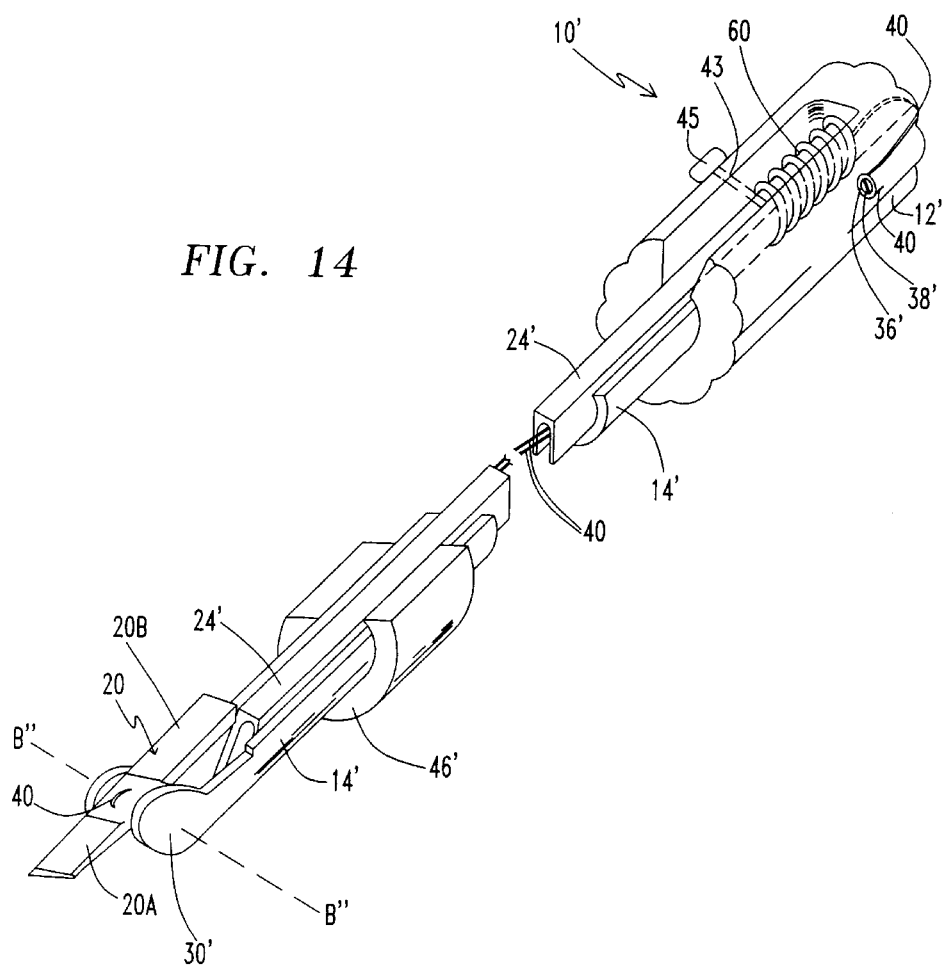
FIG. 14 shows an alternative anchor emplacement tool for an anchor of the type shown in FIGS. 10 or 11.

Turning now to FIG. 14, an alternative embodiment of a tool for emplacing an anchor according to the present invention is shown. The tool as shown in FIG. 14 is also shown as emplacing a suture anchor 20. The tool includes a handle 12' having a suture tensioner such as a grommet and screw 36', 38' about which the sutures 40 are tensioned. As in the embodiment in FIG. 1, a pushing member 24' is provided comprising a pushing channel through which the sutures 40 are threaded. The pushing channel 24' is provided in a shaft 14' having a channel to receive the pushing channel 24'. The shaft 14' is provided with a receiving receptacle 30' as in the embodiment described with respect to FIG. 1. A collar 46' is provided near the distal end of the shaft 14' and affixed to the shaft 14'. The purpose of the collar 46' is to locate the tool adjacent the bone at the perimeters of the borehole and to position the suture anchor 20 at the desired depth in the borehole in the bone.

In the handle 12' a spring 60 is provided to exert a biasing force on the pushing channel 24'. A pin 43 is disposed through an aperture in the pushing channel 24' initially to maintain the pushing channel in its proximal position. A button 45 is provided which can be actuated by the surgeon to allow the pushing channel 24' to move distally against the urging of the spring 60.

Accordingly, in use, the surgeon positions the tool in alignment with the borehole and then inserts the anchor affixed in the receiving receptacle 30' into the borehole. The surgeon then actuates the button 45 which removes the pin 43 from the opening in the pushing channel 24'. The action of the spring 60 urges the pushing channel 24' against the anchor 20, causing it to rotate about the axis B"—B". This urges the anchor 20 outwardly so that it engages with the wall of the borehole in the bone. At the same time, the handle 12' is rotated, causing the anchor 20 to cut into the wall of the borehole. The anchor will execute a spiral motion because of the two pivoting actions. The shoulder 46' will keep the pivoting receptacle 30' in a fixed location as the anchor 20 executes a spiral motion to cut into the bone to secure the anchor in the bone.

Once the anchor 20 has been secured in a position approximately perpendicular to the axis of the borehole, the tension in the sutures 40 may be removed by removing the sutures 40 from the suture tensioner 36'—38', and pulling proximally on the tool 10', thereby releasing the anchor from the pivoting receptacle 30'. The sutures can now be affixed to other tissue, for example, a ligament, or to a prosthesis.

FIGS. 15, 16 and 17*a–f* show how the anchor according to the present invention may be used to repair a ligament or to attach a prosthetic ligament, for example, for ACL repair.

Figure 15:
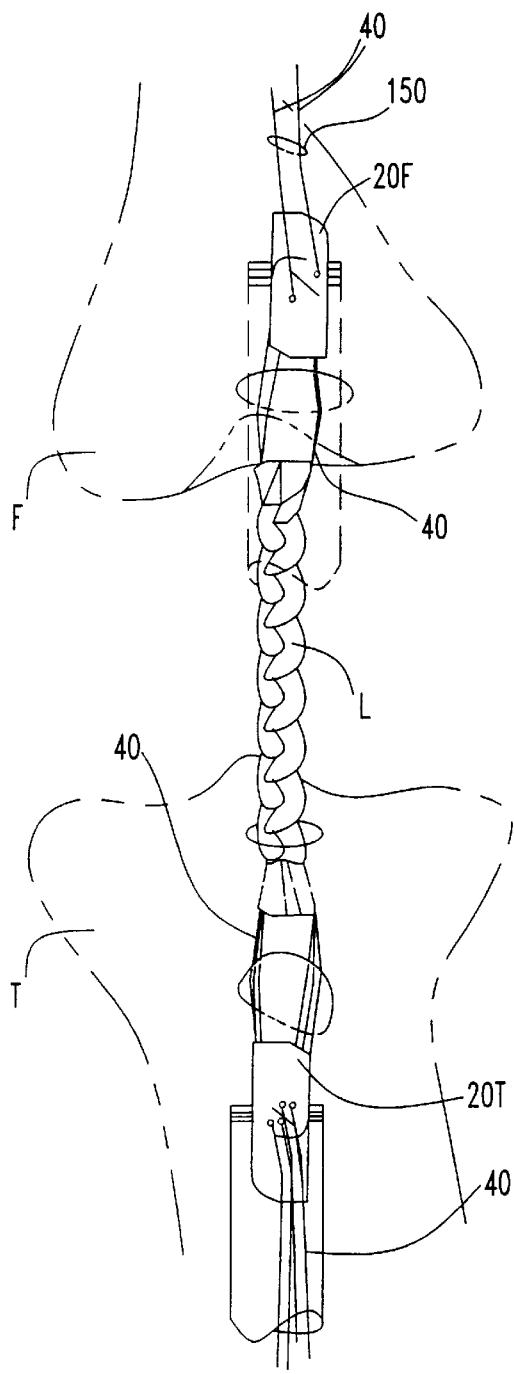
FIG. 15 shows anchors according to the present invention being used for repair of a ligament, and in particular, the ACL.

FIG. 15 shows schematically the femur F and tibia T of a human knee joint. An anchor 20F coupled to a ligament or ligament replacement L is positioned in the femur, initially aligned with a borehole made in the tibia and the femur. Anchor 20F is coupled to ligament L. The other end of ligament L is sutured to another anchor 20 T, which is positioned on the tibia.

Figure 16:
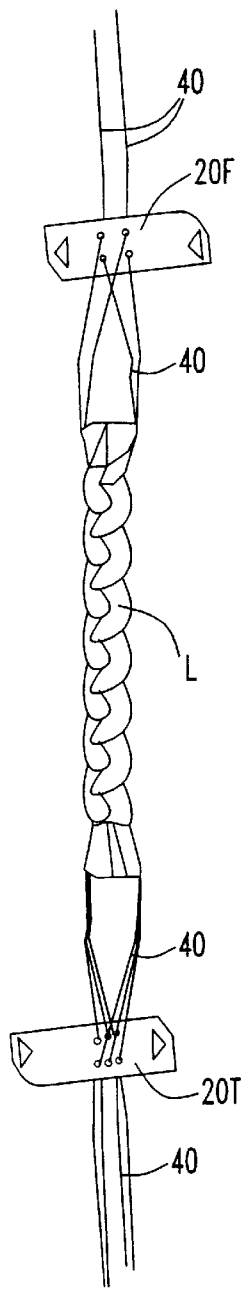
FIG. 16 shows the anchor of FIG. 15 in a perspective view after emplacement.

As shown in FIG. 15 and as also shown in FIGS. 17*a–f*, the borehole in the tibia T is made of a sufficient diameter to allow a cannulated anchor setting tool to be inserted into the borehole with the two anchors, the ligament L and the sutures contained in alignment in the canula of the insertion tool. The femur F is made with a borehole which is of a first diameter to allow the tool and the anchor 20F to be inserted therein, and which is bored through with a smaller diameter as indicated at 150, which allows the sutures 40 to be passed therethrough. FIG. 16 shows the anchors 20F and 20T after they have been rotated by 90° (along two axes, as in the other embodiments described) and have cut into the boreholes in the femur and tibia respectively. The femur and tibia are not shown in FIG. 16.

Figure 17C:
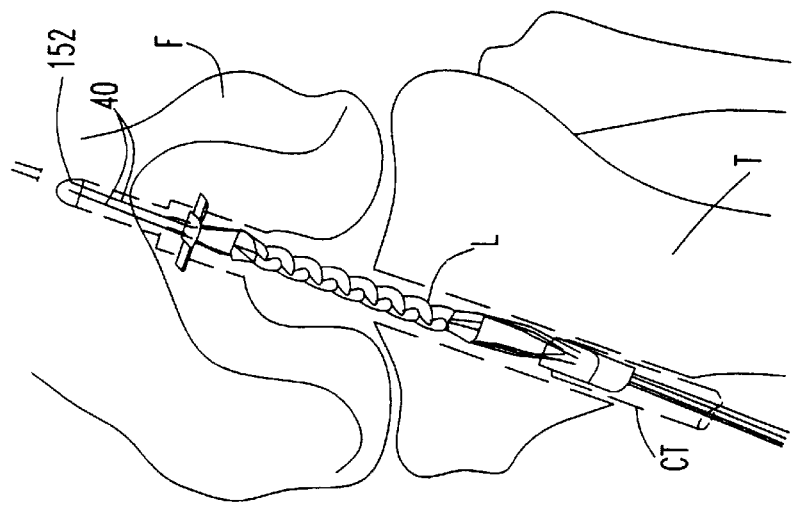
FIG. 17a–f show the steps of emplacing anchors according to the present invention to repair an ACL.
Figure 17B:
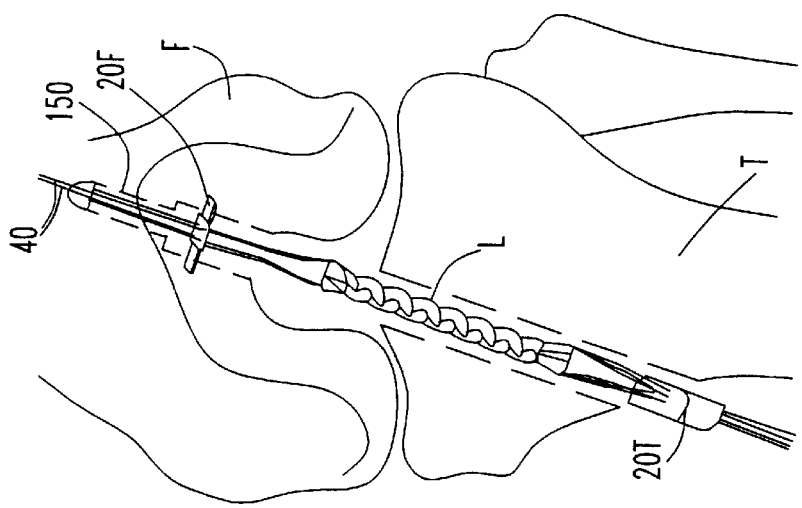
Figure 17A:
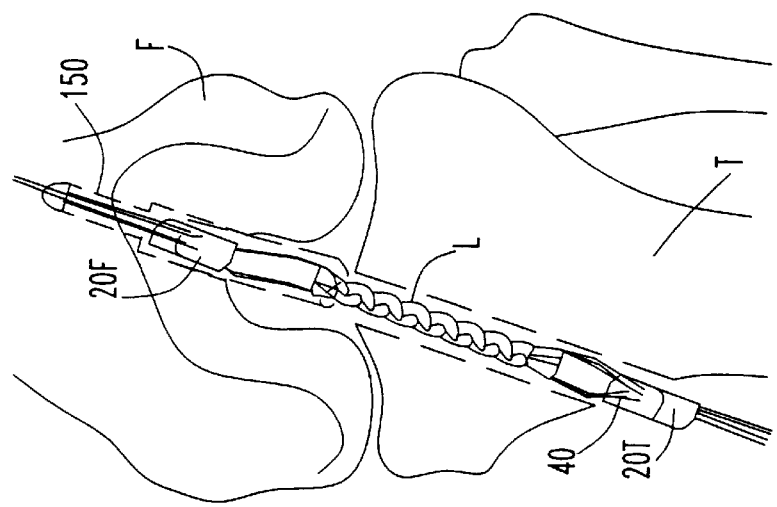

With reference to FIGS. 17*a–f*, the anchors 20T and 20F of the invention are installed for ACL repair as follows: First, a borehole is made through the tibia as shown in FIGS. 17*a–f*. Second, a borehole 150 of a smaller diameter aligned with the borehole in the tibia is made in the femur as shown. The smaller borehole 150 is then counter-drilled to have a diameter the size of the borehole in the tibia but does not extend the entire distance of the borehole in the tibia. The ligament or ligament replacement L is sutured by sutures 40 to anchor 20F and 20T. The anchors, sutures and ligament L are then placed in the canula of a cannulated tool, shown in FIG. 17*c* at ct. The tool is then inserted through the tibia opening and into the femur, at which point, as shown in FIG. 17*b*, the anchor 20F is manipulated to rotate along two axes into a position 90° to the axis of the borehole. The sutures 40 have been previously inserted completely through the borehole 150 and now extend out of the distal end of the femur borehole 150. As shown in FIG. 17*c*, the sutures 40 are tensioned and a suitable knot 152 is made in the sutures to tie the sutures off in the femur and to tension the anchor 20F.

Figure 17F:
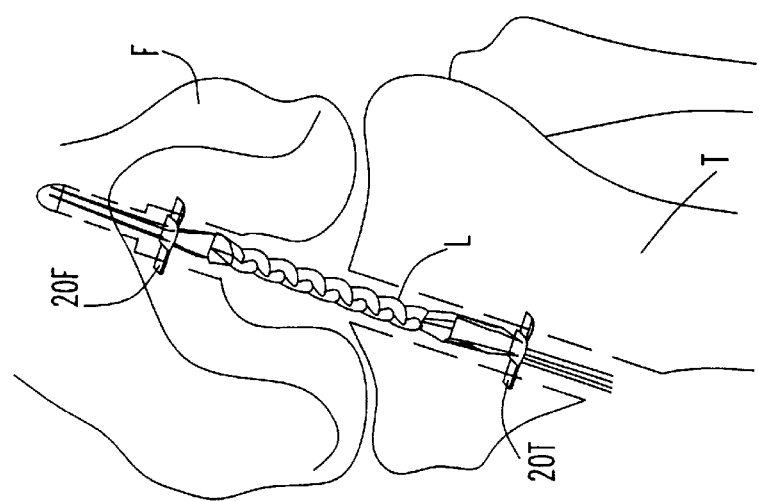
Figure 17E:
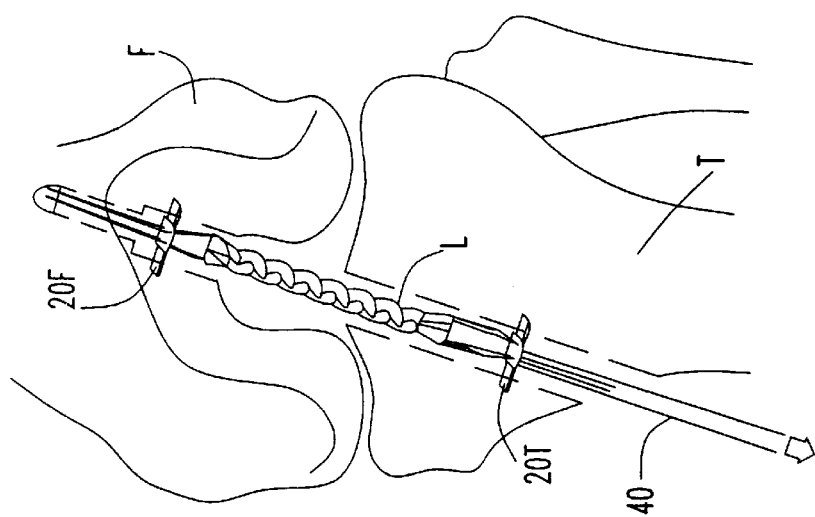
Figure 17D:
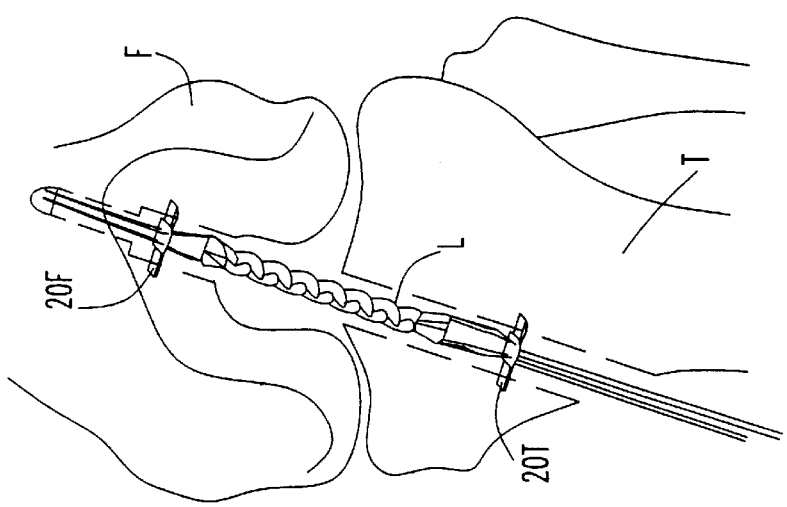

As shown in FIG. 17*d*, the tool is now actuated to manipulate the anchor 20T in the tibia to pivot the anchor along two axes in the tibia approximately 90° to the axis of the borehole. At the same time, suitable tension is applied by the tool to properly tension member L.

The tool is then withdrawn, as shown in FIG. 17*e*. A force X is exerted on the sutures 40 to tension the anchor 20T in the tibia. The sutures are then tied off and cut as shown in FIG. 17*f*. When the suture 20T in the tibia is set, a suitable tension is applied by the tool to obtain the desired tension in the ligament or ligament replacement L.

Although repair of the ACL is shown, the invention may also be used for repair of other ligaments in other skeletal joints.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A medical anchor for emplacement in a borehole in biological tissue, the anchor comprising:

a central portion;

at least one outer portion attached to the central portion, the outer portion having a cutting edge;

the anchor being adapted to be inserted in the borehole in approximate alignment with a longitudinal axis of the borehole, and further being adapted to be rotated in two axes to secure the anchor in the borehole, a first axis of rotation being aligned with the axis of the borehole and a second axis of rotation being perpendicular to the axis of the borehole, further comprising a cam surface on said anchor for engagement by a pushing member for causing said anchor to rotate about the second axis, whereby the anchor moves outwardly about the second axis so that the cutting edge cuts into a wall of the borehole and the anchor is rotated about the first axis to achieve a final position substantially perpendicular to the borehole.

2. The anchor of claim 1, wherein the anchor has two opposed outer portions, each having a cutting edge on at least one side thereof, the side of each portion having the cutting edge being opposite the side of the other portion having the cutting edge.

3. The anchor of claim 1, wherein the anchor comprises a suture anchor and further comprising at least one securement device for a suture in the central portion.

4. The anchor of claim 3, wherein the securement device comprises at least one aperture in the central portion into which a suture can be threaded.

5. The anchor of claim 4, wherein two apertures are provided in the central portion through which a suture can be threaded.

6. The anchor of claim 1, wherein each outer portion has a sloped surface terminating in a side comprising said cutting edge.

7. The anchor of claim 1, wherein the anchor has an attachment point for at least of a material and device to be attached thereto, including a prosthesis.

8. Apparatus for repairing a ligament or installing a ligament replacement, the apparatus comprising:

a first anchor for attaching to a first end of one of the ligament and ligament replacement;

a second anchor for attaching to a second end of one of the ligament and ligament replacement;

the first and second anchors being attachable to the respective first and second ends by suture;

the first and second anchors with the ligament or ligament replacement being insertable through a first borehole disposed in a first bone member into an aligned borehole in a second bone member such that the first anchor is disposed in the aligned borehole and the second anchor is disposed in the first borehole, the first anchor being rotatable about two axes in the aligned borehole, one axis being perpendicular to the aligned borehole and the other axis being aligned with the aligned borehole, the first anchor attaining a final position substantially perpendicular to the aligned borehole such that the first anchor penetrates the wall of the aligned borehole to secure the first anchor in the aligned borehole; and the second anchor being rotatable in two axes in the first borehole, one axis being perpendicular to the first borehole and the other axis being in alignment with the first borehole, the second anchor attaining a final position substantially perpendicular to the first borehole such that the second anchor penetrates the wall of the first borehole to secure the second anchor in the first borehole, thereby securing the ligament or ligament replacement between the first and second bone members.

9. A method for repairing a ligament or installing a ligament replacement, the method comprising the steps of:

providing a first anchor attached to a first end of one of the ligament and ligament replacement;

providing a second anchor attached to a second end of one of the ligament and ligament replacement;

the first and second anchors being attached to the respective first and second ends by suture;

inserting the first and second anchors with the ligament or ligament replacement with an insertion tool through a first borehole disposed in a first bone member into an aligned borehole in a second bone member such that the first anchor is disposed in the aligned borehole and the second anchor is disposed in the first borehole, rotating the first anchor with the insertion tool about two axes in the aligned borehole, one axis being perpendicular to the aligned borehole and the other axis being aligned with the aligned borehole and obtaining a final position of the first anchor substantially perpendicular to the aligned borehole such that the first anchor penetrates the wall of the aligned borehole to secure the first anchor in the aligned borehole;

rotating the second anchor with the insertion tool about two axes in the first borehole, one axis being perpendicular to the first borehole and the other axis being in alignment with the first borehole, and obtaining a final position of the second anchor substantially perpendicular to the first borehole such that the second anchor penetrates the wall of the first borehole to secure the second anchor in the first borehole, thereby securing the ligament or ligament replacement between the first and second bone members; and removing the insertion tool.

10. The method of claim 9, further comprising extending the aligned borehole through the second bone member and threading a suture tied to the first anchor through the extended aligned borehole, and further comprising tieing off said suture to tension said first anchor.

11. The method of claim 10, further comprising tieing off a suture tied to the second anchor to tension the second anchor.

12. The method of claim 9, further comprising providing tension on the ligament or ligament replacement when rotating the second anchor.

* * * * *